United States Patent
Wen

(10) Patent No.: US 8,337,199 B2
(45) Date of Patent: Dec. 25, 2012

(54) FLUID PERMEABLE DENTAL ALIGNER

(75) Inventor: Huafeng Wen, Redwood City, CA (US)

(73) Assignee: Align Technology, Inc., San Jose, CA (US)

( * ) Notice: Subject to any disclaimer, the term of this patent is extended or adjusted under 35 U.S.C. 154(b) by 766 days.

(21) Appl. No.: 11/074,300

(22) Filed: Mar. 7, 2005

(65) Prior Publication Data

US 2006/0199141 A1   Sep. 7, 2006

(51) Int. Cl.
*A61C 3/00* (2006.01)
(52) U.S. Cl. .................................................. 433/24
(58) Field of Classification Search .................. 433/24, 433/18, 6, 19, 2, 8, 215
See application file for complete search history.

(56) References Cited

U.S. PATENT DOCUMENTS

| | | |
|---|---|---|
| 1,813,583 A | 7/1931 | Rice |
| 2,037,344 A | 4/1936 | Schwartz |
| 2,138,254 A | 11/1938 | Mink |
| 2,700,218 A | 1/1955 | Lindley |
| 3,218,711 A | 11/1965 | Connan |
| 3,436,829 A | 4/1969 | Jermyn |
| 3,453,736 A | 7/1969 | Waltke |
| 3,470,614 A | 10/1969 | Kelly |
| 3,576,075 A | 4/1971 | Scott |
| 3,702,027 A | 11/1972 | Marshall et al. |
| 3,760,503 A | 9/1973 | Baskas |
| 3,890,710 A | 6/1975 | Jaeger |
| 3,905,106 A | 9/1975 | Costa et al. |
| 3,932,939 A | 1/1976 | Weissman |
| 3,937,773 A | 2/1976 | Huffman |
| 4,122,606 A | 10/1978 | Roman |
| 4,173,505 A | 11/1979 | Jacobs |
| 4,265,619 A | 5/1981 | Lucki et al. |
| 4,368,042 A | 1/1983 | Felstead et al. |
| 4,374,076 A | 2/1983 | Stephan et al. |
| 4,475,888 A | 10/1984 | Gores et al. |
| 4,494,934 A | 1/1985 | Huffman |
| 4,529,384 A | 7/1985 | Severy |
| 4,657,992 A | 4/1987 | Brennan et al. |
| 4,755,139 A | 7/1988 | Abbatte |
| 4,767,330 A | 8/1988 | Burger |
| 4,798,534 A | 1/1989 | Breads |
| 4,828,117 A | 5/1989 | Panzera et al. |
| 4,856,991 A | 8/1989 | Breads |
| 4,936,862 A | 6/1990 | Walker |
| 4,943,237 A | 7/1990 | Bryan |
| 5,011,405 A | 4/1991 | Lemchen |
| 5,035,613 A | 7/1991 | Breads |
| 5,055,039 A | 10/1991 | Abbatte |
| 5,059,118 A | 10/1991 | Breads |
| 5,131,844 A | 7/1992 | Maranccio et al. |
| 5,186,623 A | 2/1993 | Breads |
| 5,273,429 A | 12/1993 | Rekow |
| 5,338,198 A | 8/1994 | Wu |
| 5,340,309 A | 8/1994 | Robertson |
| 5,342,202 A | 8/1994 | Deshayes |
| 5,368,478 A | 11/1994 | Andreiko |
| 5,382,164 A | 1/1995 | Stern |

(Continued)

*Primary Examiner* — Todd Manahan
*Assistant Examiner* — Yogesh Patel

(57) ABSTRACT

A shell-shaped dental aligner for producing predetermined movement in a patient's tooth includes a shell portion comprising a fluid-permeable material, an outer surface of the shell portion, and an inner surface of the shell portion, the inner surface to be in contact with the patient's tooth. The fluid-permeable material can allow fluid to communicate between the patient's tooth and the vicinity of the outer surface.

23 Claims, 2 Drawing Sheets

U.S. PATENT DOCUMENTS

| | | |
|---|---|---|
| 5,452,219 A | 9/1995 | Dehoff |
| 5,466,152 A | 11/1995 | Walter |
| RE35,263 E | 6/1996 | Silva et al. |
| 5,549,476 A | 8/1996 | Stern |
| 5,587,912 A | 12/1996 | Andersson |
| 5,607,305 A | 3/1997 | Andersson |
| 5,616,899 A | 4/1997 | Recigno |
| 5,645,421 A | 7/1997 | Slootsky |
| 5,788,489 A | 8/1998 | Huffman |
| 5,879,158 A | 3/1999 | Doyle |
| 5,911,580 A | 6/1999 | Sharp et al. |
| 5,927,984 A | 7/1999 | Lin |
| 5,975,893 A | 11/1999 | Chishti |
| 6,217,325 B1 | 4/2001 | Chishti |
| 6,227,850 B1 | 5/2001 | Chishti |
| 6,227,851 B1 | 5/2001 | Chishti |
| 6,261,098 B1 | 7/2001 | Persson |
| 6,299,440 B1 | 10/2001 | Phan |
| 6,309,215 B1 | 10/2001 | Phan |
| 6,423,252 B1 * | 7/2002 | Chun et al. .............. 264/28 |
| 6,425,759 B1 | 7/2002 | Cronin |
| 6,497,574 B1 | 12/2002 | Miller |
| 6,499,997 B2 | 12/2002 | Chishti |
| 6,514,074 B1 | 2/2003 | Chishti |
| 6,516,080 B1 * | 2/2003 | Nur .............. 382/109 |
| 6,524,101 B1 | 2/2003 | Phan |
| 6,554,611 B2 | 4/2003 | Chishti |
| 6,572,372 B1 | 6/2003 | Phan |
| 6,582,227 B2 | 6/2003 | Phan |
| 6,582,229 B1 | 6/2003 | Miller |
| 6,602,070 B2 | 8/2003 | Miller |
| 6,607,382 B1 * | 8/2003 | Kuo et al. .............. 433/6 |
| 6,621,491 B1 | 9/2003 | Baumrind |
| 6,626,666 B2 | 9/2003 | Chishti et al. |
| 6,626,669 B2 | 9/2003 | Zegarelli |
| 6,629,840 B2 | 10/2003 | Chishti |
| 6,633,789 B1 | 10/2003 | Nikolskiy |
| 6,665,570 B2 | 12/2003 | Pavloskaia |
| 6,682,346 B2 | 1/2004 | Chishti |
| 6,685,469 B2 | 2/2004 | Chishti |
| 6,685,470 B2 | 2/2004 | Chishti |
| 6,688,886 B2 | 2/2004 | Hughes |
| 6,699,037 B2 | 3/2004 | Chishti |
| 6,705,861 B2 | 3/2004 | Chishti |
| 6,722,880 B2 | 4/2004 | Chishti |
| 6,726,478 B1 | 4/2004 | Isiderio |
| 6,729,876 B2 | 5/2004 | Chishti |
| 6,846,179 B2 | 1/2005 | Chapouland et al. |
| 6,882,894 B2 | 4/2005 | Durbin et al. |
| 6,913,462 B2 | 7/2005 | Honstein et al. |
| 6,923,649 B2 | 8/2005 | Oswald et al. |
| 6,981,874 B2 | 1/2006 | Allred et al. |
| 7,040,897 B2 | 5/2006 | Fischer |
| 7,153,135 B1 | 12/2006 | Thomas |
| 7,186,760 B2 | 3/2007 | Rudo |
| 7,250,611 B2 | 7/2007 | Aguirre et al. |
| 2001/0002310 A1 * | 5/2001 | Chishti et al. .............. 433/24 |
| 2001/0027401 A1 | 10/2001 | Klein |
| 2001/0037248 A1 | 11/2001 | Klein |
| 2002/0015934 A1 * | 2/2002 | Rubbert et al. .............. 433/29 |
| 2002/0017998 A1 | 2/2002 | Price |
| 2002/0150855 A1 | 10/2002 | Chishti et al. |
| 2002/0187451 A1 * | 12/2002 | Phan et al. .............. 433/6 |
| 2003/0002089 A1 | 1/2003 | Vadnais et al. |
| 2003/0003416 A1 | 1/2003 | Chishti et al. |
| 2003/0039940 A1 * | 2/2003 | Miller .............. 433/24 |
| 2003/0203334 A1 | 10/2003 | Hedge et al. |
| 2003/0207227 A1 | 11/2003 | Abolfathi |
| 2004/0063060 A1 | 4/2004 | Meyers et al. |
| 2004/0109783 A1 | 6/2004 | Prasad et al. |
| 2004/0115587 A1 * | 6/2004 | Breining et al. .............. 433/24 |
| 2004/0197728 A1 * | 10/2004 | Abolfathi et al. .............. 433/24 |
| 2004/0234929 A1 | 11/2004 | Fischer et al. |
| 2005/0003319 A1 | 1/2005 | Kuo |
| 2005/0186150 A1 | 8/2005 | Allred |
| 2005/0186526 A1 * | 8/2005 | Stewart et al. .............. 433/24 |
| 2006/0093982 A1 | 5/2006 | Wen |
| 2006/0093987 A1 | 5/2006 | Wen |
| 2006/0093992 A1 | 5/2006 | Wen |
| 2006/0093993 A1 | 5/2006 | Wen |
| 2006/0127838 A1 | 6/2006 | Liu et al. |
| 2006/0127850 A1 | 6/2006 | Wen |
| 2006/0127851 A1 | 6/2006 | Wen |
| 2006/0134580 A1 | 6/2006 | Raby et al. |
| 2006/0275736 A1 | 12/2006 | Wen et al. |

* cited by examiner

FLUID PERMEABLE DENTAL ALIGNER

TECHNICAL FIELD

This application generally relates to the field of dental care, and more particularly to the field of orthodontics.

CROSS-REFERENCES TO RELATED INVENTIONS

The present invention is also related to concurrently filed (Mar. 7, 2005) and commonly assigned U.S. patent application Ser. No. 11/074,299, entitled "Producing Physical Dental Arch Model Having Individually Adjustable Tooth Models" by Liu et al., U.S. patent application Ser. No. 11/074,301, entitled "Dental Aligner for Providing Accurate Dental Treatment" by Liu et al., U.S. patent application Ser. No. 11/074,297, entitled "Producing Wrinkled Dental Aligner for Dental Treatment" by Liu et al., and U.S. patent application Ser. No. 11/074,298, entitled "Disposable Dental Aligner" by Huafeng Wen.

The present invention is also related to commonly assigned U.S. patent application Ser. No. 10/979,823, titled "Method and apparatus for manufacturing and constructing a physical dental arch model" by Huafeng Wen, filed Nov. 2, 2004, U.S. patent application Ser. No. 10/979,497, titled "Method and apparatus for manufacturing and constructing a dental aligner" by Huafeng Wen, filed Nov. 2, 2004, U.S. patent application Ser. No. 10/979,504, titled "Producing an adjustable physical dental arch model" by Huafeng Wen, filed Nov. 2, 2004, and U.S. patent application Ser. No. 10/979,824, titled "Producing a base for physical dental arch model" by Huafeng Wen, filed Nov. 2, 2004. The disclosure of these related applications are incorporated herein by reference.

The present invention is also related to commonly assigned U.S. patent application Ser. No. 11/013,152, titled "A base for physical dental arch model" by Huafeng Wen, filed Dec. 14, 2004, commonly assigned U.S. patent application Ser. No. 11/012,924, titled "Accurately producing a base for physical dental arch model" by Huafeng Wen, filed Dec. 14, 2004, commonly assigned U.S. patent application Ser. No. 11/013,145, titled "Fabricating a base compatible with physical dental tooth models" by Huafeng Wen, filed Dec. 14, 2004, commonly assigned U.S. patent application Ser. No. 11/013,156, titled "Producing non-interfering tooth models on a base" by Huafeng Wen, filed Dec. 14, 2004, commonly assigned U.S. patent application Ser. No. 11/013,160, titled "System and methods for casting physical tooth model" by Huafeng Wen, filed Dec. 14, 2004, commonly assigned U.S. patent application Ser. No. 11/013,159, titled "Producing a base for accurately receiving dental tooth models" by Huafeng Wen, and filed Dec. 14, 2004, commonly assigned U.S. patent application Ser. No. 11/013,157, titled "Producing accurate base for dental arch model" by Huafeng Wen, filed Dec. 14, 2004. The disclosure of these related applications are incorporated herein by reference.

BACKGROUND

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is difficult for a human being to accurately develop a visual three-dimensional image of an orthodontic structure due to the limitations of human sight and the physical structure of a human mouth. In addition, it is difficult to accurately estimate three-dimensional wire bends (with an accuracy within a few degrees) and to manually apply such bends to a wire. Further, it is difficult to determine an ideal bracket location to achieve the desired orthodontic structure based on the mental images. It is also difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art, relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No; 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Kuroda et al. (1996) Am. J. Orthodontics 110:365-369 describes a method for laser scanning a plaster dental cast to produce a digital image of the cast. See also U.S. Pat. No. 5,605,459. U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the arch is described in U.S. Pat. Nos. 5,342,202 and 5,340,309.

Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

The key to efficiency in treatment and maximum quality in results is a realistic simulation of the treatment process. Today's orthodontists have the possibility of taking plaster models of the upper and lower arch, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per arch that covers all brackets and relevant portions of every tooth. Using such a transfer tray guarantees a very quick and yet precise bonding using indirect bonding.

U.S. Pat. No. 5,431,562 to Andreiko et al. describes a computerized, appliance-driven approach to orthodontics. In this method, first certain shape information of teeth is acquired. A uniplanar target arcform is calculated from the shape information. The shape of customized bracket slots, the bracket base, and the shape of the orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, Align Technology, Inc. began offering transparent, removable aligning devices as a new treatment modality in orthodontics. In this system, an impression model of the dentition of the patient is obtained by the orthodontist and shipped to a remote appliance manufacturing center, where it is scanned with a CT scanner. A computer model of the dentition in a target situation is generated at the appliance manufacturing center and made available for viewing to the orthodontist over the Internet. The orthodontist indicates changes they wish to make to individual tooth positions. A revised virtual model is provided for the orthodontist to review, until the target situation is agreed upon. A series of removable aligning devices or shells are manufactured and delivered to the orthodontist. The shells will move the patient's teeth to the desired or target position.

U.S. Pat. No. 6,699,037 describes an improved methods and systems for repositioning teeth from an initial tooth arrangement to a final tooth arrangement. Repositioning is accomplished with a system comprising a series of appliances configured to receive the teeth in a cavity and incrementally reposition individual teeth in a series of successive steps, usually including at least four successive steps, often including at least ten steps, sometimes including at least twenty-five steps, and occasionally including forty or more steps. Most often, the methods and systems will reposition teeth in from ten to twenty-five successive steps, although complex cases involving many of the patient's teeth may take forty or more steps. The successive use of a number of such appliances permits each appliance to be configured to move individual teeth in small increments, typically less than 2 mm, preferably less than 1 mm, and more preferably less than 0.5 mm. These values refer to the maximum linear translation of any point on a tooth as a result of using a single appliance. The movements provided by successive appliances, of course, will usually not be the same for any particular tooth. Thus, one point on a tooth may be moved by a different distance as a result of the use of one appliance and thereafter moved by a different distance and/or in a different direction by a later appliance.

The individual appliances preferably comprise a polymeric shell having the teeth-receiving cavity formed therein, typically by molding Each individual appliance is configured so that its tooth-receiving cavity has a geometry corresponding to an intermediate or end tooth arrangement intended for that appliance. That is, when an appliance is first worn by the patient, certain of the teeth will be misaligned relative to an undeformed geometry of the appliance cavity. The appliance, however, is sufficiently resilient to accommodate or conform to the misaligned teeth, and will apply sufficient resilient force against such misaligned teeth in order to reposition the teeth to the intermediate or end arrangement desired for that treatment step.

The fabrication of aligners using a stereo lithography process is disclosed in US Pat. No. 6,471,511 and 6,682,346. The stereo lithography process builds the aligner layer by layer, and may use a different aligner mold at each stage of the treatment There is therefore a long felt need for practical, effective and efficient methods to produce a dental aligner.

A long recognized issue is that the aligning devices do not allow oxygen to pass through them. A typical treatment takes about 18 to 24 months and during this interval, the cervical lines of the patient wearing such appliances remain covered for the major part of the day without letting air to pass through them. Oxygen cannot reach the cells of the cervical lines. Air trapped inside the aligning appliances also cannot get out easily. Anaerobic bacteria such as Fusobacterium and Actinomyces often thrive in an oxygen-deprived environment and produce volatile sulfur compounds (VSC) as byproducts, which can result in bad breath (halitosis) and hygiene problems in the patient's mouth.

SUMMARY OF THE INVENTION

The present invention has been devised to substantially eliminate the foregoing problems and is to provide methods and apparatus to manufacture and construct the physical dental arch model. Implementations of the system may include one or more of the following.

In one aspect, the present invention relates to a shell-shaped dental aligner for producing predetermined movement in a patient's tooth, comprising:
a shell portion comprising a fluid-permeable material;
an outer surface of the shell portion; and
an inner surface of the shell portion, the inner surface to be in contact with the patient's tooth, wherein the fluid-permeable material can allow fluid to communicate between the patient's tooth and the vicinity of the outer surface.

In another aspect, the present invention relates to a method for treating a patient's teeth, comprising determining an initial configuration of the patient's teeth;
determining a final configuration of the patient's teeth;
designing a movement path for at least one of the patient's teeth from the initial configuration to the final configuration;
dividing the movement path into a plurality of successive treatment steps, each having a target configuration for the patient's teeth; and
producing a dental aligner comprising a fluid-permeable material to move the patient's teeth to the target configuration associated with a treatment step.

In yet another aspect, the present invention relates to a system for treating a patient's teeth, comprising:
a computer configured to determine a target configuration for the patient's teeth; and
an apparatus configured to produce a dental aligner comprising a shell portion that comprises a fluid-permeable material, an outer surface, and an inner surface to be in contact with one of the patient's teeth, wherein the fluid-permeable material can allow fluid to communicate between the one of the patient's teeth and the vicinity of the outer surface and the dental aligner is configured to move the patient's teeth to the target configuration.

Embodiments may include one or more of the following advantages. The present invention provides fluid permeable dental aligning devices for patients that allow oxygen to pass through to the patient's teeth and cervical lines in the arch. The increase oxygen concentration under the dental aligning devices can overcome the problem of bacteria growth under the aligner device in the conventional aligner systems.

Another advantage of the present invention is that it provides porous channels for saliva to pass through the dental aligners. Saliva plays a critical role in controlling halitosis and bacterial growth. Saliva contains proteins, carbohydrates, and immunoglobulins that interfere with bacterial metabolism and bacterial adherence to oral surfaces. Saliva as a solvent can control the mouth odor in the oral chemical environment. As a result the mouth odor and oral hygiene of the patient who wears the dental aligner are improved.

Yet another advantage of the present invention is that the capability of passing oxygen and saliva not only improves the patient's oral hygiene but also allowing the patient clean the aligner less frequently, which is more convenient for the patient. The less frequent removal and wearing can also lengthen the usage lifetime and the effectiveness of the dental aligning devices.

The details of one or more embodiments are set forth in the accompanying drawing and in the description below. Other features, objects, and advantages of the invention will become apparent from the description and drawings, and from the claims.

BRIEF DESCRIPTION OF THE DRAWINGS

The accompanying drawing, which are incorporated in and form a part of this specification, illustrate embodiments of the invention and, together with the description, serve to explain the principles of the invention.

DETAILED DESCRIPTION OF EMBODIMENTS

The present invention intends to overcome the above-described difficulties experienced by the transparent removable aligning devices. In one aspect, removable dental aligners are fabricated using a fluid-permeable material to allow fluid to communicate between the outer surface and the inner surface of the dental aligner. The fluid-permeable material comprises pores or micro-channels to allow air and liquid to permeate through to the patient's teeth, which suppresses the growth of the VSC producing bacteria in the patient's mouth and improves the patient's oral hygiene. Air trapped in the dental aligner can also be circulated out continuously, which also helps to suppress the unnatural growth of anaerobic bacteria and associated halitosis. Oxygenated saliva liquid passing through the permeable material to the cervical line of the patient's teeth reduces the amount of bacterial VSCs, which reduces the risks for halitosis.

Figure 1:
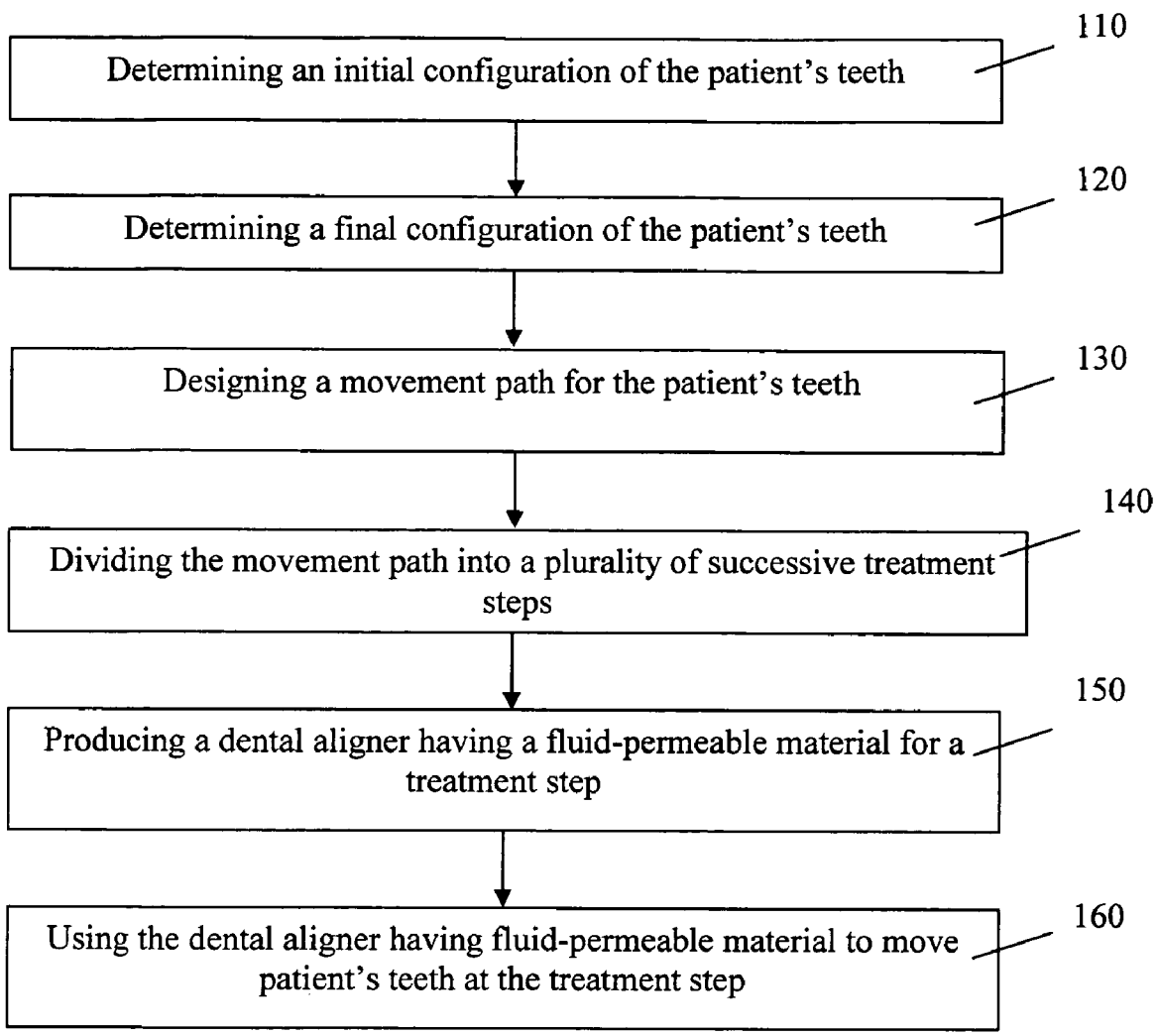
FIG. 1 illustrates an orthodontic process for using a dental aligner comprising a fluid-permeable material.

FIG. 1 illustrates a process for producing a dental aligner made of a fluid permeable material. In an orthodontic treatment, an initial configuration of the patient's arch is first determined in step 110. The patient's arch can include one or more teeth in the upper jaw and lower jaw. The configuration includes positions and orientations of the patient's teeth. The initial configuration can be obtained by first producing a negative impression of the patient's arch and then scanning the surfaces of the negative impression by 3D positional measurement devices. The dentist analyzes the initial configuration of the patient's teeth and determines the final configuration of the patient's teeth in step 120. The final configuration comprises the positions and the orientations of the patient's teeth after the corrective treatment process.

The dentist will then design a movement path for each of the teeth involved in step 130. A typical orthodontic treatment is usually divided into a plurality of successive treatment steps in step 140. One or more specifically designed disposable dental aligners are used to move the patient's teeth to a pre-designed target configuration. The treatment at the step is intended to produce incremental amounts of changes in positions or orientations that are within the comfort tolerance of the patient as well as the performance of the dental aligner.

Figure 2:
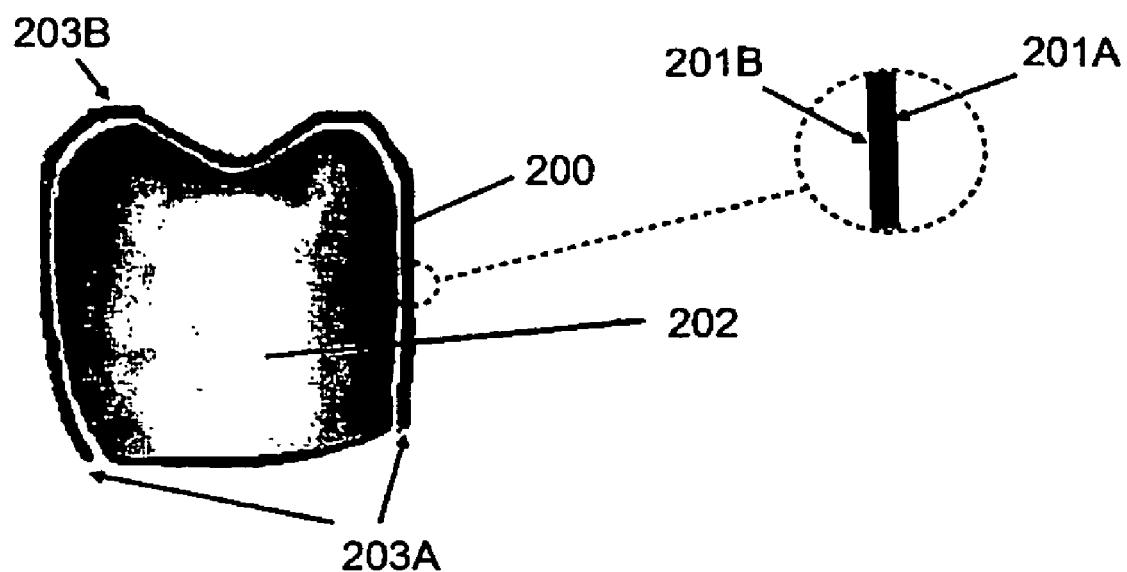
FIG. 2 illustrates a shell-shaped dental aligner in accordance with an embodiment of the invention.

As shown in FIG. 2, the removable dental aligner is typically shell shaped and can be worn by a patient over his or her dental arch to produce corrective movement in a patient's teeth. The dental aligner typically includes a shell portion 200 an outer surface of the shell portion 201A, and an inner surface of the shell portion 20IB. The inner surface will be in contact with the patient's teeth (202). The shell-shaped dental aligner can further include a bottom portion 203A to be placed near the gingival of the patient's tooth and a tip portion 203B on the opposite side of the bottom portion.

In accordance with the present invention, fluid-permeable dental aligners allow air or liquid to communicate between the patient's tooth and the vicinity of the outer surface. Dental aligners are fabricated to achieve the same incremental teeth movement at that particular step 150. The dental aligners can be molded using fluid-permeable materials in a casting chamber. The mold can be a negative impression produced by a physical dental arch model that comprises the patient's tooth models that are configured in the target configuration for the specific treatment step. The dental aligners can also be fabricated by a CNC based machine in response to a digital aligner model.

Details of producing a physical dental arch model and associated base are disclosed in the above referenced and commonly assigned U.S. patent application Ser. No. 10/979,823, titled "Method and apparatus for manufacturing and constructing a physical dental arch model" by Huafeng Wen, filed Nov. 2, 2004, U.S. patent application Ser. No. 10/979,497, titled "Method and apparatus for manufacturing and constructing a dental aligner" by Huafeng Wen, filed Nov. 2, 2004, U.S. patent application Ser. No. 10/979,504, titled "Producing an adjustable physical dental arch model" by Huafeng Wen, filed Nov. 2, 2004, and U.S. patent application Ser. No. 10/979,824, titled "Producing a base for physical dental arch model" by Huafeng Wen, filed Nov. 2, 2004. The disclosure of these related applications are incorporated herein by reference.

The effects of the dental aligners having permeable materials can be simulated by computer modeling. The progressive teeth configurations in an orthodontic treatment can be represented by a digital dental arch model. The disposable aligners can be simulated by a digital aligner model. The computer simulation helps to determine the number of steps needed for each treatment and the material properties of the dental aligners. In particular, the properties of the permeable materials can be simulated to predict and optimize the fluid permeation function of the dental aligner. The fluid permeability of the dental aligner can be optimized by varying the diameters and the density of the pores. The preferred material properties and structures are predicted. Materials and fabrication processes can be experimented and selected to achieve the desired properties and structures in the dental aligners.

The pore density and diameters can be of uniform or non-uniform distribution across the dental aligners. For example, the pore density can be higher at the portion of the shell-shaped dental aligner along cervical lines to allow extra air and liquid communication to the cervical lines of the patient's teeth to prevent bacteria growth. The hardness of the dental aligners can also be varied depending on the intended length of use of a particular dental aligner. In addition, the fluid permeation properties can also depend on the patient life style, his or her use pattern of the dental aligner, and the climate in which he or she wears the dental aligning devices. These optimized properties will improve the patient comfort and convenience in using the dental aligner having fluid-permeable material for corrective orthodontic treatment in step 160.

The dental aligners can include wrinkled surfaces to enhance the strength and sustainability of the dental aligner. Details of wrinkled dental aligners and the fabrications are disclosed in the commonly assigned and concurrently filed U.S. patent application titled "Dental aligner for providing accurate dental treatment" by Liu et al and U.S. patent application titled "Producing wrinkled dental aligner for dental treatment" by Liu et al., the disclosures of which are herein incorporated by reference.

The dental aligners comprising fluid-permeable material can also be disposable. A plurality of disposable dental aligners having substantially identical shape can be produced for a single step of the treatment. The use of multiple disposable dental aligners allows a disposable dental aligner to be replaced before it is relaxed and deforms. This assures the uniform application of force the patient's teeth over time and improves the accuracy of the treatment. Because of their effectiveness, the disposable dental aligners can shorten the overall treatment time. The disposable dental aligners is also more comfortable for the patient to wear because of the smaller granular movements induced by each disposable dental aligner. Details of the manufacturing of disposable dental aligners are disclosed in the concurrently filed and commonly assigned U.S. patent application Ser. No. 11/074,298 titled "Disposable Dental Aligner", the disclosure of which is herein incorporated by reference.

A variety of fluid-permeable materials are compatible with the disclosed methods and system. The fluid-permeable materials can include polymeric materials prepared by copolymerizing styrene and divinylbenzene (DVB). Very small pores or 'micropores' can be formed in such process as a result of DVB tying together linear chains of styrene at various points. The "degree of cross-linking" is determined by the percentage of DVB present. The "degree of cross-linking" in turn determines the size of the pores. A 10% cross-linked polymer contains 10% DVB and has somewhat smaller pores than a 2% cross-linked polymer since the additional DVB creates additional linkage points making the average distance between those points smaller. However, as cross-linking is reduced pore size increases, the physical stability of the polymer decreases. Fluid permeability and strength therefore need to be co-optimized in designing dental aligners. Pore sizes are typically less than 30 Å in diameter and fairly uniform distributed.

Another type of porous polymer was independently developed in the late 1950s by scientists at The Dow Chemical Company and at Rohm and Haas. These materials have come to be called "macroporous polymers", and pores are formed independently of cross-linking. Polymerization takes place in the presence of "porogens". Porogens are substances that are soluble in monomers, but insoluble in formed polymers. Thus, as polymerization proceeds, pores are formed in the spaces where porogens are found. Pore diameters are typically greater than 50 Å, with some polymers having pore diameters as great as 2000 to 4000 Å. Most polymers, however, contain pores in the 100 Å to 300 Å range. Pore size distributions tend to be somewhat broad, particularly in polymers having large average pore sizes. These materials are characterized by irregular shaped-pores that terminate within the polymer body. Macroporous polymers are usually prepared with a high degree of cross-linking (typically 30% or greater) to lend greater physical stability to the resulting material and to yield polymers that do not swell in solvents. The discovery of this route to synthesizing polymers led to materials with much larger pore size and much higher porosity than preceding microporous materials; however total porosity rarely exceeds 50%. Details of this type of porous polymers are disclosed in U.S. Pat. No. 3,322,695 titled "Preparation of Porous Structures" by Alfrey et al., and U.S. Pat. No. 4,224,415 titled "Polymerization Processes and Products Therefrom" by Meitzner et al., the disclosure of these U.S. patents are incorporated herein by reference.

Other porous materials include porous polymer structures known as "high internal phase emulsions" ("HIPE") that are disclosed in U.S. Pat. No. 4,522,953 "Low Density Porous Cross-linked Polymeric Materials and their Preparation and Use as Carriers for Included Liquids" by Barby et al. and U.S. Pat. No. 5,583,162 titled "Polymeric Microbeads and Method of Preparation" by Li et al. The disclosures of these U.S. patents are incorporated herein by reference.

Another approach of making fluid permeable dental aligners is to mix a base sheet material with small granules of a low-density compound (usually a form of plastic). The low-density compound has a lower sublimation point than the base material. The sheet of material mixture is then placed in a heated container over a mould. Air is pumped out. The appliance is separated from the mould and is subjected to high temperature and/or pressure, which results in the sublimation of the granular low-density material. The molecules of the material are converted to gaseous forms (in case of plastic, formaldehyde) and leave behind pores large enough to let gas and/or liquid molecules pass through.

Pores can also be made in the dental aligner by laser beams with extraordinary power stability. The diameters of the holes can be controlled in the range between 40-400 µm at a perforation speed as high as 500,000 holes per second. The density and pore sizes can be directly controlled by a computer in response to a dental aligner model.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A fluid-permeable dental aligner for producing predetermined movement of one or more teeth in a dental arch of a patient, comprising:
    a shell-shaped structure configured to fit over said dental arch, said shell-shaped structure having an inner surface configured to be in contact with said one or more teeth and an opposing outer surface configured to be exposed to a mouth cavity of the patient;
    said shell-shaped structure comprising a porous portion of sufficient hardness to produce movement of said one or more teeth, said porous portion configured to be in contact with said one or more teeth and comprising one or more pores passing from said inner surface to said outer surface, said one or more pores being configured to communicate air and saliva between said one or more teeth and said mouth cavity.

2. The fluid-permeable dental aligner of claim 1, wherein said shell-shaped structure is configured to overlap gingiva adjacent to said one or more teeth, and wherein said one or more pores are configured to communicate air and saliva between said mouth cavity and said gingiva.

3. The fluid-permeable dental aligner of claim 1, wherein the shell shaped structure comprises a porous polymeric material.

4. The fluid-permeable dental aligner of claim 1, wherein the pores are drilled by a laser beam.

5. The fluid-permeable dental aligner of claim 1, wherein the one or more pores have diameters in the range of 50 Å to 400 µM.

6. The fluid-permeable dental aligner of claim 1, comprising a non-uniform distribution of said pores.

7. The fluid-permeable dental aligner of claim 6, wherein a spatial density of said pores on said shell-shaped structure is greater at a location adjacent to a cervical line than a location not adjacent to the cervical line.

8. A method for treating a patient's teeth, comprising:
    determining an initial configuration of the patient's teeth in a dental arch;
    determining a final configuration of the patient's teeth in the dental arch;
    designing a movement path for at least one of the patient's teeth from the initial configuration to the final configuration;
    dividing the movement path into a plurality of successive treatment steps, each having a target configuration for the patient's teeth; and
    producing a fluid-permeable dental aligner to move the patient's teeth toward the target configuration associated with a treatment step, said fluid-permeable dental aligner comprising a shell-shaped structure configured to fit over said dental arch, said shell-shaped structure having an inner surface configured to be in contact with the patient's teeth and an opposing outer surface configured to be exposed to a mouth cavity of the patient;
    wherein producing said fluid-permeable dental aligner comprises forming a porous portion of sufficient hardness to produce movement of one or more of the patient's teeth, said porous portion configured to be in contact with said one or more teeth and comprising one or more pores passing from said inner surface to said outer surface, said one or more pores being configured to communicate air and saliva between said patient's one or more teeth and said mouth cavity.

9. The method of claim 8, wherein forming said one or more pores comprises drilling holes with a laser beam in a dental-aligner material.

10. The method of claim 8, wherein the fluid-permeable dental aligner comprises a porous polymeric material.

11. The method of claim 8, wherein the target configuration comprises the target positions and the target orientations of one or more of the patient's teeth.

12. The method of claim 8, further comprising molding the fluid permeable dental aligner in a casting chamber.

13. The method of claim 8, wherein the pores are formed by subliming a low density granular compound by pressure and elevated temperature in a base material.

14. The method of claim 8, further comprising:
    performing a computer simulation to predict a fluid permeation function representing a degree of communication of air and/or liquid through the pores of the fluid-permeable dental aligner.

15. The method of claim 14, further comprising:
    optimizing a the degree of communication of air and/or liquid of the dental aligner by varying one or more of the diameter of said pores and the distribution of said pores.

16. The method of claim 15, wherein the degree of communication of air and/or liquid depends on a climate of a location in which the dental aligner is to be worn.

17. The method of claim 15, wherein the degree of communication of air and/or liquid depends on an expected usage pattern of the dental aligner by the patient.

18. The method of claim 8, further comprising:
    providing a greater distribution of said pores in the dental aligner adjacent to a cervical line.

19. A system for treating a patient's teeth, comprising:
    a computer configured to determine a target configuration for the patient's teeth in a dental arch;

an apparatus configured to produce a fluid-permeable dental aligner configured to move the patient's teeth toward the target configuration;

one or more fluid-permeable dental aligners produced by the apparatus, said dental-aligners comprising a shell-shaped structure configured to fit over said dental arch, said shell-shaped structure having an inner surface configured to be in contact with said patient's teeth and an opposing outer surface configured to be exposed to a mouth cavity of the patient, said shell-shaped structure comprising a porous portion of sufficient hardness to produce movement of one or more of the patient's teeth, said porous portion configured to be in contact with said one or more teeth and comprising one or more pores passing from said inner surface to said outer surface, said one or more pores being configured to communicate air and saliva between said one or more teeth and said mouth cavity.

20. The method of claim 19, wherein the fluid-permeable dental aligner comprises a porous polymeric material.

21. The system of claim 19, wherein the apparatus is configured to drill holes by a laser beam in a dental-aligner material to form the fluid-permeable dental aligner.

22. The system of claim 19, wherein the apparatus is configured to mold the fluid-permeable dental aligner using a casting chamber.

23. The system of claim 19, wherein the apparatus is configured to form one or more pores having diameters in the range of 50 Å to 400 μM

* * * * *